(12) United States Patent
Miller et al.

(10) Patent No.: US 6,210,727 B1
(45) Date of Patent: Apr. 3, 2001

(54) METHOD AND MEANS OF CONTROLLING A FOOD EXTRUDER AS A FUNCTION OF BULK DENSITY OF THE EXTRUDED PRODUCT

(75) Inventors: Donovan Z. Miller, Forest Grove, OR (US); Henry Z. Miller, Machesney Park, IL (US)

(73) Assignee: American Extrusion International, Corp., South Beloit, IL (US)

( * ) Notice: Subject to any disclaimer, the term of this patent is extended or adjusted under 35 U.S.C. 154(b) by 0 days.

(21) Appl. No.: 09/495,711

(22) Filed: Feb. 1, 2000

(51) Int. Cl.[7] ................................. A23P 1/00; G01N 9/00
(52) U.S. Cl. .................... 426/231; 73/433; 73/863.51; 99/487; 177/50; 177/145; 426/516
(58) Field of Search ..................... 426/231, 516, 426/448; 99/487, 516; 73/433, 863.51, 863.57; 177/50, 145

(56) References Cited

U.S. PATENT DOCUMENTS

| | | | | |
|---|---|---|---|---|
| 5,143,738 | * | 9/1992 | Nordin | 426/231 |
| 5,423,216 | * | 6/1995 | Kitamura et al. | 73/433 |
| 5,563,384 | * | 10/1996 | Marlow et al. | 73/433 |

* cited by examiner

*Primary Examiner*—George C. Yeung
(74) *Attorney, Agent, or Firm*—James Van Santen

(57) ABSTRACT

A bulk density sampling method and device whereby formed product is flowed through a vertically disposed passage of pre-determined size. The passage is temporarily obstructed to collect and weigh a known volume of product upon which to base a calculation of bulk density and the generation of a control signal for regulating a multi-tasking processor to constantly monitor, control, and display speed, head gap position, temperature, feed rate and target moisture.

15 Claims, 3 Drawing Sheets

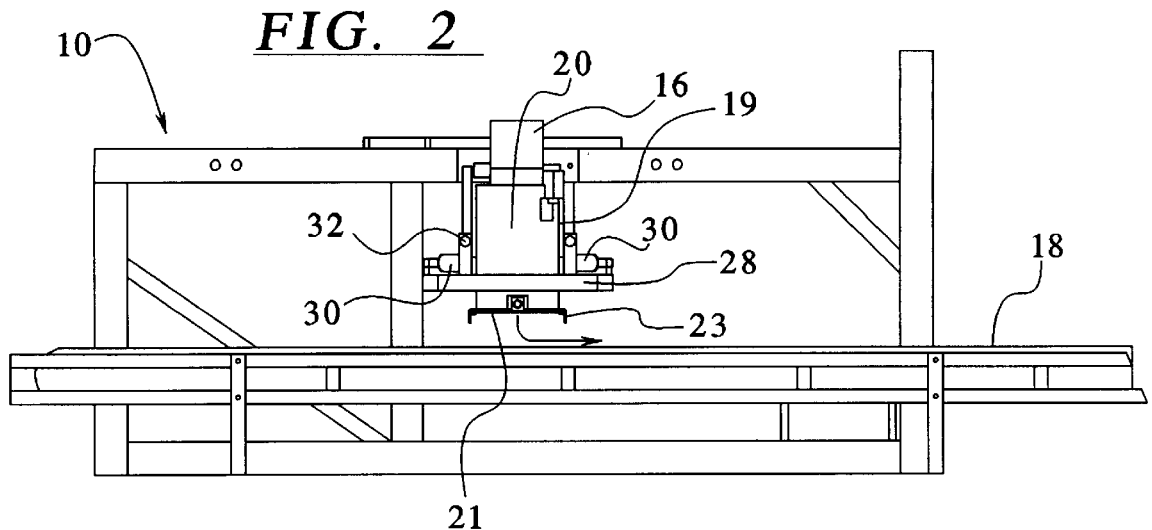
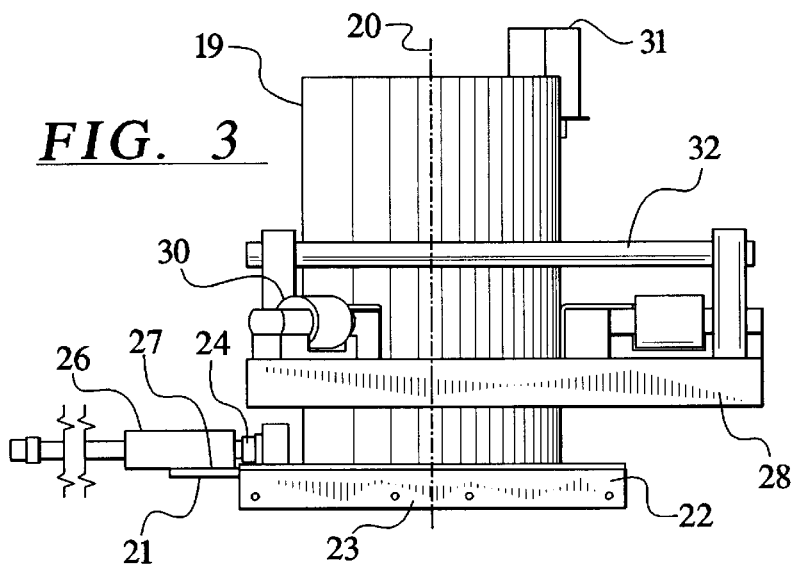
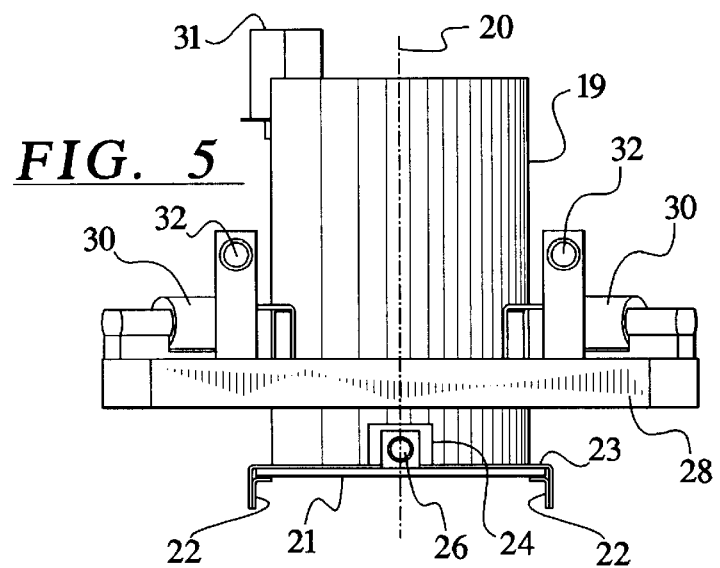

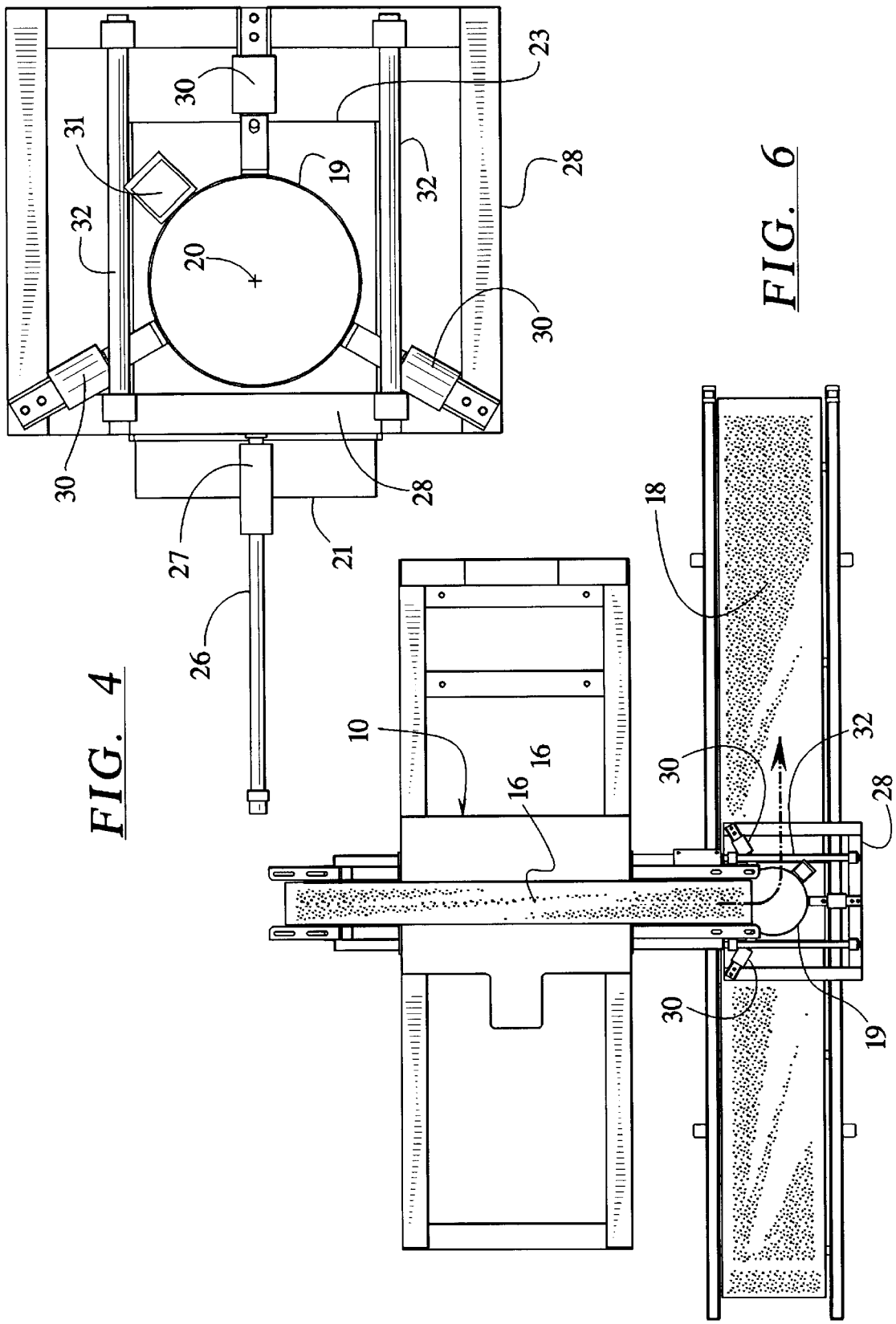

METHOD AND MEANS OF CONTROLLING A FOOD EXTRUDER AS A FUNCTION OF BULK DENSITY OF THE EXTRUDED PRODUCT

BACKGROUND OF THE INVENTION

1. Field of the Invention

This invention relates generally to machines for extruding food products, for example, from corn meal, and more particularly relates to a method and means for controlling such a machine with improved bulk density sampler techniques for selective sampling of extruded material flowing in a material processing stream.

2. The Prior Art

The prior art is exemplified by machines of the type manufactured and sold by the assignee of the present application, one exemplification of which is disclosed in U.S. Pat. No. 5,143,738 issued Sep. 1, 1992 and entitled "Computerized Food Product Extrusion Machine and Method."

Bulk density sampler arrangements occur in the prior art. For example, reference is made to U.S. Pat. No. 5,563,384 issued Oct. 8, 1996 wherein a receptacle of known volume is intermittently interposed into and out of a stream of flowing material to gather a supply of the formed extruded material. After the receptacle is withdrawn from the product stream, special instrumentalities must be provided to measure the weight of the gathered formed product. First, the receptacle is weighed when it is empty and it is weighed again when it is full. Means are provided to restore the sample product into product stream.

Additionally, the mechanism must be provided with a housing for protection of the sampling assembly and receptacle from the product stream and other debris which may be present in the operating environment.

SUMMARY OF THE PRESENT INVENTION

The present invention contemplates the utilization of a method and means of controlling a food extruder wherein raw material is extruded to make formed product. The formed product is discharged and flowed into a material processing stream.

At one point in the stream the formed product flows through a permanent stationary confined calibrated passage of prescribed known volumetric size. One end of the calibrated passage is selectively obstructed so that formed product will be collected and accumulate in the confined passage. Sensing means are utilized to sense when a quantum of accumulated formed product has been collected in the calibrated passage equal to the pre-determined known volume, whereupon the collected known volume of formed product is weighed to generate a control signal which is a function of the of the bulk density of the collected formed product.

The control signal is then fed to a programmable logic computer (PLC) which controls the operation of the extruder to constantly monitor, control and display speed, head gap position, temperature, feed rate and target moisture.

The end of the permanent stationary collection passage is simply cleared of the temporary obstruction so that the formed product accumulated within the passage, as well as the formed product continuously flowing through the product stream, may proceed downstream without further incident in the material processing stream.

DESCRIPTION OF THE DRAWINGS

FIG. 2 is a fragmentary front elevational view of the bulk density measuring mechanism provided in accordance with the principles of the present invention.

FIG. 3 is a side elevational view of the mechanism of FIG. 2.

FIG. 4 is a top plan view of the mechanism of FIG. 2.

FIG. 5 is a rear elevational view of the mechanism of FIG. 2.

FIG. 6 is a top plan view, in section, of the food extruder and bulk density measuring mechanism taken generally in the plane of line V—V of FIG. 1.

DESCRIPTION OF THE PREFERRED EMBODIMENTS

Figure 1:
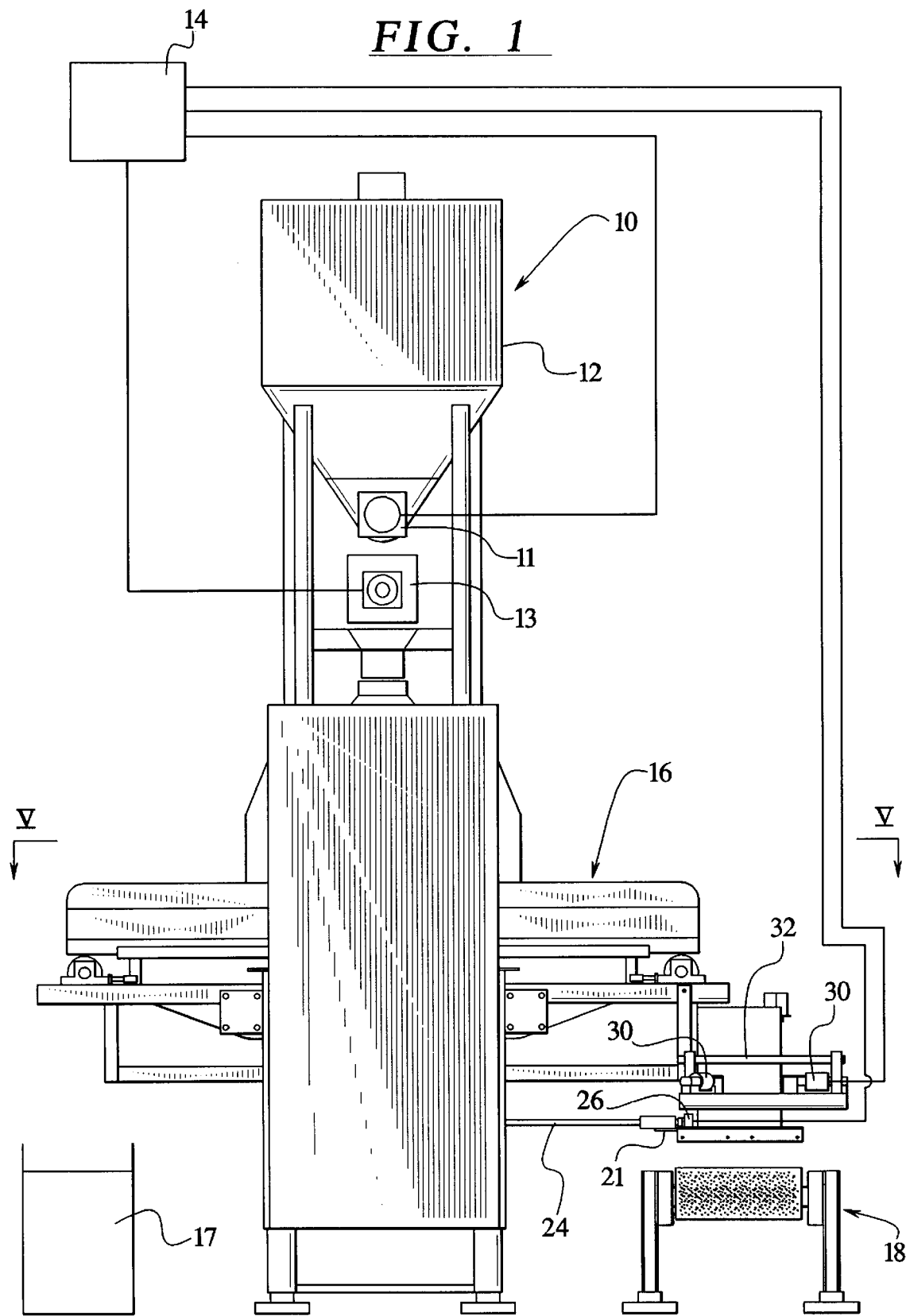
FIG. 1 is an elevational view, with parts broken away, and with schematic wiring control circuitry added, and showing a food extruder for producing cellular food product, but having a bulk density arrangement provided in accordance with the principles of the present invention, and capable of practicing the method of this invention.

Referring to FIG. 1 of the drawings, there is shown an exemplary form of a food extruder 10 of the type wherein raw material is extruded to make formed product. The extruder 10 has a number of basic components which together with one another provide the environment in which the specific improvements of the present disclosure find their greatest utility.

First of all, raw material, such as corn grain, is stored or fed in a hopper, for example, a vibrating stainless steel hopper 12, from which the raw material is transferred to a positive auger metering feeder 11, at which time the raw material is humidified under the control of a moisture control system 13 regulated by computer means having a programmable logic controller 14 (PLC).

From the metering feeder 11, the raw material is conveyed via a mixer screw, sometimes referred to as a pre-blender, into an extruder unit. In the extruder unit, the raw material is processed by being extruded through an adjustable head gap, also under the control of the PLC 14. The PLC 14 adjusts the temperature at the point of extrusion and, automatically brings the head gap into precise position for maximizing product quality. With digital read out to thousandths of an inch, consistent quality product is assured. A resultant formed product, or cellular food product, exits the extruder unit via an outlet.

The PLC preferably utilizes a code which directs the execution of sampling bulk density in a random manner to obtain optimum statistical process control.

Vibrator means provided on the hopper 12 assist in moving grain to the conduit having an outlet in which is situated a moisture probe comprising one or more dielectric sensors by means of which the moisture content of the grain is measured. A water delivery system in the moisture control system 13 adds water to the grain to bring the moisture content thereof up to an optimum required level for accomplishing quality extrusion.

In operation the moisture control system 13, or the probe of that system, generates an analog moisture content signal which is sent to the PLC 14 in which the signal is compared with the preselected desired moisture content. A differential signal resulting from the comparison is digitized and is used to control the delivery of water to the metering feeder.

The positive auger metering feeder 11 comprises a helical screw that is driven at infinitely adjustable variable speeds, and which is also under the control of the PLC 14. The amount of water flow delivered by the water delivery system is controlled in proportion to the quantum of grain transported out from the hopper 12 to the extruder 10 so that the formed product has the requisite characteristics of shape, form and density.

In operation, the formed product is discharged continuously onto a take-away conveyor 16 to form a material processing stream. The take-away conveyor 16 is reversible and the machine as described has an automatic start-up. The PLC 14 prepares raw material, adjusts the head gap, feeds the raw material, controls the temperature and reverses the discharge belt of the take-away conveyor 16 so irregular product is caught in a waste bin 17. When satisfactory product is achieved, the discharge belt of the take-away conveyor is engaged in the forward direction.

In the running operation of the machine, the PLC 14 constantly monitors, controls and displays the parameters of speed, head gap position, temperature, feed rate and target moisture.

In order to accomplish an efficient and effective control of the extruding machine 10, it is necessary and essential that the PLC 14, receive frequent and accurate reports of data which reflect operating conditions. Food manufacturing processes typically require continuous monitoring in order to produce an acceptable food product of high quality. Thus, in the manufacture of products formed by extrusion, for example, snack foods, pastas, cereals and pet food, a good indicator of the product quality is the final density of the formed product.

Frequent samples must be taken of the formed product in the material processing stream. Such samples must be measured and analyzed. The information developed can be utilized by the algorithm programmed into the PLC 14 to adjust and control the process.

In accordance with the principles of the present invention, we have discovered an entirely new and different concept of bulk density sampling which is particularly adaptable to a food extruding machine. Referring now to FIGS. 1–6 of the drawings, an exemplification of a bulk sampling device capable of practicing the steps of the method contemplated is shown. The extruding machine 10 has a take-away conveyor 16 which is intended to remove the formed product from the immediate locale of the extruding machine 10. It does this by delivering the formed product in the form of a material processing stream to a transport conveyor 18 which carries the formed product in the material processing stream to a packaging, or shipping, point of utilization.

At a first point in the material processing stream downstream of the take-away conveyor 16 on the extruding machine 10, a point preferably situated between the take-away conveyor 16 and the transport conveyor 18, we contemplate gravitationally flowing the formed product material processing stream through a permanent, stationary, vertical, confined, collection passage of uniform cross-section and of a prescribed size in length. Thus, it is, in effect, a longitudinally extending tube can be considered as being calibrated to be of a pre-determined known volumetric size at any selectively chosen level.

While it is conceivable that such a passage could be of any known regular geometric cross-sectional configuration, there is illustrated in the drawings a volume collection cylinder 19 disposed to provide a uniform cylindrical passage extending on a vertical axis 20 which intersects the plane of the take-away conveyor 16 as well as the plane of the transport conveyor 18. Accordingly, formed product in the material processing stream at the first point in the stream will fall gravitationally, and continuously, from the take-away conveyor 16 downwardly in the direction of the vertical axis 20, through the volume cylinder 19 and onto the transport conveyor 18.

In the non-sampling mode of operation of the bulk density sampling device, the formed product in the material processing stream freely passes through the bulk density sampler without any interruption in a normal manner of product delivery.

In order to achieve a sampling mode, there is provided a controlled slide gate 21 which is movably supported in slide runners 22 carried on a support frame 23 at the lower end of the volume collection cylinder 19. The slide gate 21 is selectively actuated by an air cylinder 24 having an operating piston 26 coupled to the slide gate 21 as at 27. Thus, the slide gate 21 can be moved horizontally, i.e., at right angles to the vertical axis 20, from a first inoperative position laterally displaced from the volume collection cylinder 19, to a second obstructing position extending across the bottom of the volume collection cylinder 19 and completely closing the vertical passage through the volume collection cylinder 19. When so moved to the second obstructing position, formed product will be collected and will begin to accumulate in the volume cylinder 19.

There is an upper support frame 28 connected to the extruder and such frame 28 has one or more load cells 30 which support the volume collection cylinder 19 and the lower support frame 23, which, in turn carries the slide gate assembly. Adjustment rods for the frame 28 are shown at 32.

A photo cell 31 is attached, or mounted, in such a manner as to determine when the collection cylinder 19 is full. In the present embodiment, the photo cell 31 is attached to the top of the collection cylinder 19. The lower frame 23 together with the volume collection cylinder 19 and the air cylinder 24 are suspended in such a manner that the programmable logic controller (PLC) 14 takes a reading of the gross weight of such components as are supported by the load cells 30 while empty, and in a non-sampling mode, commonly referred to as a tare weight.

In the sampling mode, the slide gate 21 is actuated by the PLC 14. When formed product is accumulating in the volume collection cylinder 19, the electronic photo eye, or photo cell, 31 "watches" the top of the volume collection cylinder 19 to sense when it has been filled to a predetermined level. When a "full" condition is sensed, the take-away conveyor 16 is momentarily stopped so that it stops sending product for approximately three (3) seconds while the load cells 30 determine the final weight of the filled volume collection cylinder 19. The tare weight is subtracted from the filled weight, thereby giving the net weight by means of which the bulk density of the formed product can be automatically calculated. On the basis of such calculation, a control signal is generated and the PLC 14 makes such adjustments as may be required to automatically regulate head gap position, feed rate and target moisture.

While minor modifications might be suggested by those versed in the art, it should be understood that we wish to embody within the scope of the patent warranted hereon all such modifications as come within the scope of our contribution to the art.

We claim as our invention:

1. A method of controlling a food extruding machine wherein raw material is extruded to make formed product, which includes the steps of:
   (1) discharging the formed product,
   (2) flowing the discharged product in a material processing stream,
   (3) at one point in the stream flowing the formed product through a permanent stationary confined passage of pre-determined, pre-selected volumetric size, (4) selectively obstructing one end of the passage to accumulate and collect formed product in the passage, (5) sensing the quantum of accumulated formed product in the passage when a predetermined pre-selected volume of formed product has been collected in the passage, (6) weighing the collected pre-selected volume of formed product to calculate and generate a control signal which is a function of the bulk density of the formed product, and (7) utilizing the control signal in a programmable logic computer which controls, monitors, and displays speed, head gap position, temperature, feed rate and target moisture to maintain quality product.

2. The method of claim 1, further including adding the step of (8) clearing said one end of the permanent stationary passage so that the weighed formed product resumes downstream flow and proceeds in the material processing stream.

3. In a programmable logic computer means for monitoring, controlling and displaying speed, head gap position, temperature, feed rate and target moisture in a food extruding machine of the type wherein raw material is extruded to form a product, the improvement of, conveyor means flowing formed product discharged from the extruding machine in the form of a material processing stream, measuring means forming a vertical passage of pre-determined dimensional size disposed and arranged so that said material processing stream is gravitationally directed through said vertical passage, said measuring means prescribing a volumetric capacity of pre-selected volume when said passage is filled with product between first and second vertically spaced points along the length of said vertical passage, gate means at said first of said first and second vertically spaced points for temporarily and selectively blocking the lower end of said vertical passage, thereby to accumulate and collect product in the passage, sensing means at said second vertically spaced point above said first point sensing when a specified pre-selected volume of product has been collected in said vertical passage, weighing means weighing the collected pre-selected volume of product and generating a control signal which is a function of the bulk density of the collected product, and computer control means responsive to said control signal generated by said weighing means to operate said extruding machine.

4. The method of claim 1 wherein in step (3) the material processing stream is flowed gravitationally through a confined passage which is vertically disposed.

5. The method of claim 2 wherein in step (8) the product gravitationally resumes its flow in the material processing stream.

6. A bulk density sampling apparatus comprising, passage forming means forming a vertically extending, open-ended, uniform cross-sectional configuration, confined, passage of predetermined volumetric size, through which a flow of a material processing stream is directed, gate means at one end of said passage forming means to selectively block the flow of a material processing stream flowing gravitationally through said passage, sensing means disposed at an opposite end of said passage forming means to sense the accumulation of a pre-selected volume of material collected in the blocked passage, and weighing means for generating a control signal responsive to the net weight of the accumulated collected pre-selected volume of material which is a function of the bulk density of the material.

7. The bulk density sampling apparatus as defined in claim 6 wherein said passage forming means comprises a cylindrical tube of uniform cross-sectional size.

8. The method of claim 1 wherein the programmable logic computer has a code which directs the execution of bulk density sampling in a random manner to obtain optimum statistical process control.

9. A bulk density sampling apparatus comprising, passage forming means forming a vertically extending, passage of uniform cross-sectional configuration of pre-determined volumetric size, through which a flow of a material processing stream is gravitationally directed, gate means at the lower end of said passage forming means to selectively block the flow of a material processing stream flowing gravitationally through said passage, means at the upper end of said passage forming means temporarily stopping flow of the material processing stream upon accumulation of a pre-selected volume of material in said passage, and weighing means for generating a control signal responsive to the net weight of the accumulated collected pre-selected volume of material which is a function of the bulk density of the material.

10. An extruding machine, comprising take-away conveyor means for flowing formed product discharged in the form of a material processing stream, measuring means forming a passage of uniform cross-sectional size disposed vertically at one point in the material processing stream through which the stream passes gravitationally, gate means at the lower end of said measuring means to selectively block the bottom of said passage, thereby to accumulate and collect product from the material processing stream in the passage, weighing means to weigh said measuring means and said gate means to obtain gross weight and tare weight thereof after and before said passage has been filled with said product and from which a bulk density signal can be computed and generated, and a programmable logic computer responsive to said bulk density signal for controlling the extruding machine to insure product quality.

11. The extruding machine as defined in claim 10 wherein said computer controls said gate means and said conveyor means and has a code which directs the execution of bulk density sampling in a random manner to obtain optimum statistical process control.

12. The extruding machine as defined in claim 11, further including moisture control means controlled by said programmable logic computer for introducing and controlling water flow in proportion to the volume of product processed by said extruding machine.

13. An extruding machine of the type wherein raw material is extruded to make formed product and from which the product is discharged and flowed into a material processing stream, said machine having delivery means comprising a take away conveyor forming a first point in the material processing stream to move the formed product away from the machine, a permanent stationary volume collection passage means forming a second point in the material processing stream and comprising a vertically disposed cylindrical tube of uniform cross-section extending longitudinally on a vertical axis which intersects the path of the take-away conveyor, support means connected to said extruding machine and having one or more load cells supporting said collection passage means, said support means carrying a lower support means having a sliding gate mechanism with an air cylinder and a movable piston coupled to a gate which selectively blocks the lower end of said passage means, an electronic photo cell supported in such a manner as to watch and detect when a predetermined volume of product in the material processing stream has accumulated and collected in said passage means when said gate is in the blocking position, weighing means associated with said load cells to weigh said support means and said lower support means carried thereby including the passage forming means and the sliding gate mechanism, thereby to facilitate obtaining a tare weight and a gross filled weight, of the collected product from which the bulk density of the collected product can be computed, and a programmable logic computer (PLC) responsive to variations in the bulk density which PLC controls the extruding machine to constantly monitor, control and display speed, head gap position, temperature and feed rate in the operation of the extruding machine.

14. The extruding machine of claim 13, further including a moisture control system operatively controlled by said PLC and regulating the amount of water delivered to the extrusion machine in proportion to the volume of raw material processed by the extruder.

15. The extruding machine of claim 13, further including a transport conveyor in register with the lower end of said passage means receiving product from the material processing stream exiting the passage means for further processing and transport.

\* \* \* \* \*